(12) United States Patent
Jang et al.

(10) Patent No.: US 11,642,108 B2
(45) Date of Patent: May 9, 2023

(54) MAGNETIC ROBOT

(71) Applicant: IUCF-HYU (Industry-University Cooperation Foundation Hanyang University), Seoul (KR)

(72) Inventors: Gunhee Jang, Seoul (KR); Eun Soo Jung, Seoul (KR); Jae Kwang Nam, Goyang-si (KR)

(73) Assignee: Industry-University Cooperation Foundation, Hanyong University, Seoul (KR)

( * ) Notice: Subject to any disclaimer, the term of this patent is extended or adjusted under 35 U.S.C. 154(b) by 636 days.

(21) Appl. No.: 16/633,888

(22) PCT Filed: Apr. 3, 2018

(86) PCT No.: PCT/KR2018/003911
§ 371 (c)(1),
(2) Date: Jan. 24, 2020

(87) PCT Pub. No.: WO2019/022340
PCT Pub. Date: Jan. 31, 2019

(65) Prior Publication Data
US 2020/0205793 A1  Jul. 2, 2020

(30) Foreign Application Priority Data
Jul. 25, 2017  (KR) ........................ 10-2017-0094167

(51) Int. Cl.
*A61B 10/02* (2006.01)
*A61B 34/37* (2016.01)
(Continued)

(52) U.S. Cl.
CPC .......... *A61B 10/0266* (2013.01); *A61B 10/04* (2013.01); *A61B 34/37* (2016.02); *A61B 34/73* (2016.02); *A61B 2010/045* (2013.01)

(58) Field of Classification Search
CPC ..... A61B 10/0266; A61B 10/04; A61B 34/37; A61B 34/73; A61B 2010/045;
(Continued)

(56) References Cited

U.S. PATENT DOCUMENTS

2004/0064067 A1* 4/2004 Ward ................. A61B 10/0275
600/562
2006/0028751 A1* 2/2006 Takeuchi ............. G02B 26/085
(Continued)

FOREIGN PATENT DOCUMENTS

JP    2002-102347 A    4/2002
JP     5399253 B2      1/2014
(Continued)

OTHER PUBLICATIONS

International Search Report for PCT/KR2018/003911 dated Jul. 16, 2018 [PCT/ISA/210].

*Primary Examiner* — Rene T Towa
(74) *Attorney, Agent, or Firm* — Sughrue Mion, PLLC

(57) ABSTRACT

A magnetic robot is provided. The magnetic robot comprises: a moving part which could be moved by means of a control of an external magnetic field; and an inspection part which is coupled to a frontal end of the moving part, wherein the inspection part comprises: a body provided with a tissue sampling needle at the frontal end thereof; a cover for covering the body; and a cover-moving part for moving the cover between a first position and a second position, wherein in the case where the cover is positioned in the first position, the tissue sampling needle is housed within the cover, and in the case where the cover is positioned in the second position, the tissue sampling needle is exposed to the outside of the cover.

5 Claims, 5 Drawing Sheets

(51) Int. Cl.
*A61B 10/04* (2006.01)
*A61B 34/00* (2016.01)
(58) Field of Classification Search
CPC .............. A61B 34/30; A61B 2034/303; A61B 2010/0208; A61B 10/0233
See application file for complete search history.

(56) References Cited

U.S. PATENT DOCUMENTS

| | | | | |
|---|---|---|---|---|
| 2007/0255300 | A1* | 11/2007 | Vanhiel | A61B 5/1513 606/181 |
| 2010/0069943 | A1* | 3/2010 | Roe | A61B 5/15194 606/181 |
| 2016/0367236 | A1* | 12/2016 | Leeflang | A61M 25/0127 |
| 2018/0000501 | A1* | 1/2018 | Baym | A61B 34/32 |

FOREIGN PATENT DOCUMENTS

| | | |
|---|---|---|
| KR | 10-2011-0016004 A | 2/2011 |
| KR | 10-2014-0026957 A | 3/2014 |
| KR | 101394798 B1 | 5/2014 |
| KR | 101462588 B1 | 11/2014 |
| KR | 10-2015-0022206 A | 3/2015 |
| WO | 2008/105393 A1 | 9/2008 |

* cited by examiner

[Fig. 1]
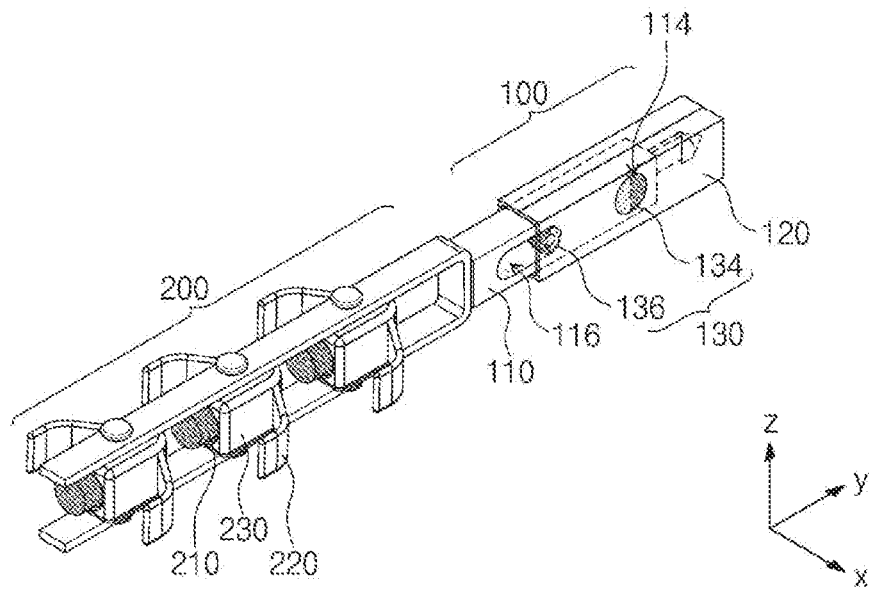
[Fig. 2]
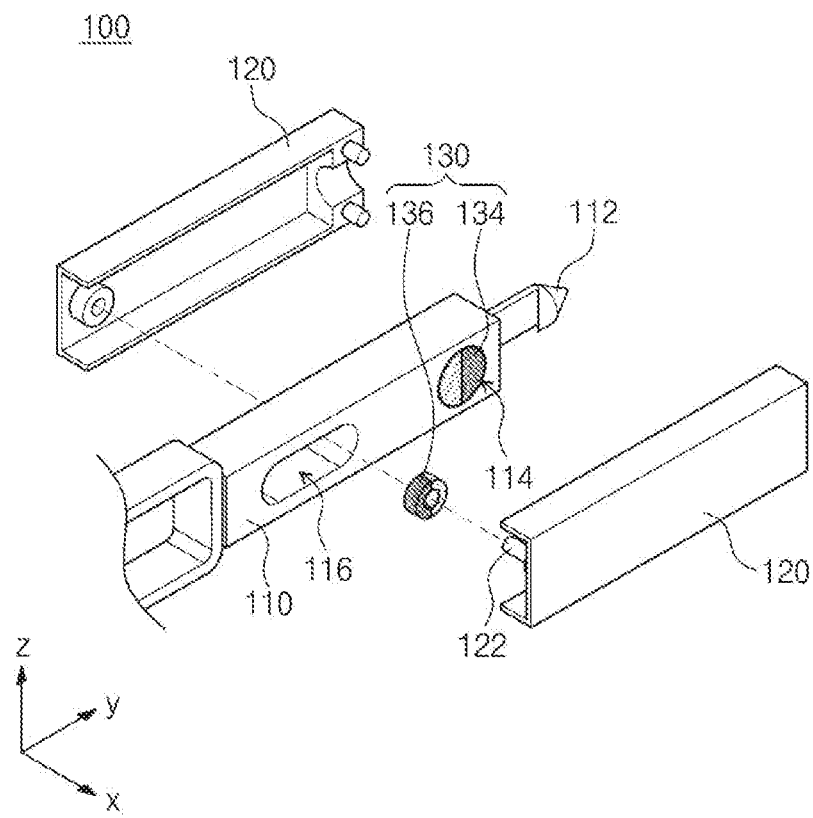

[Fig. 3(A)]
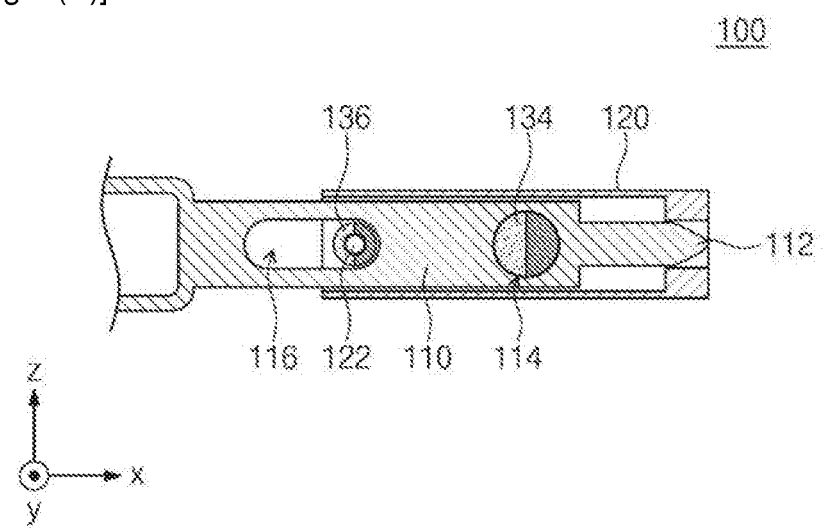
[Fig. 3(B)]
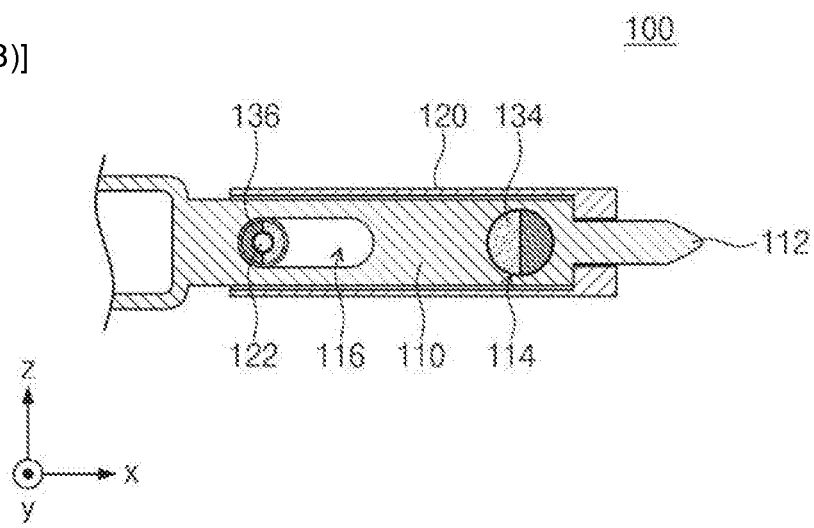

[Fig. 4]
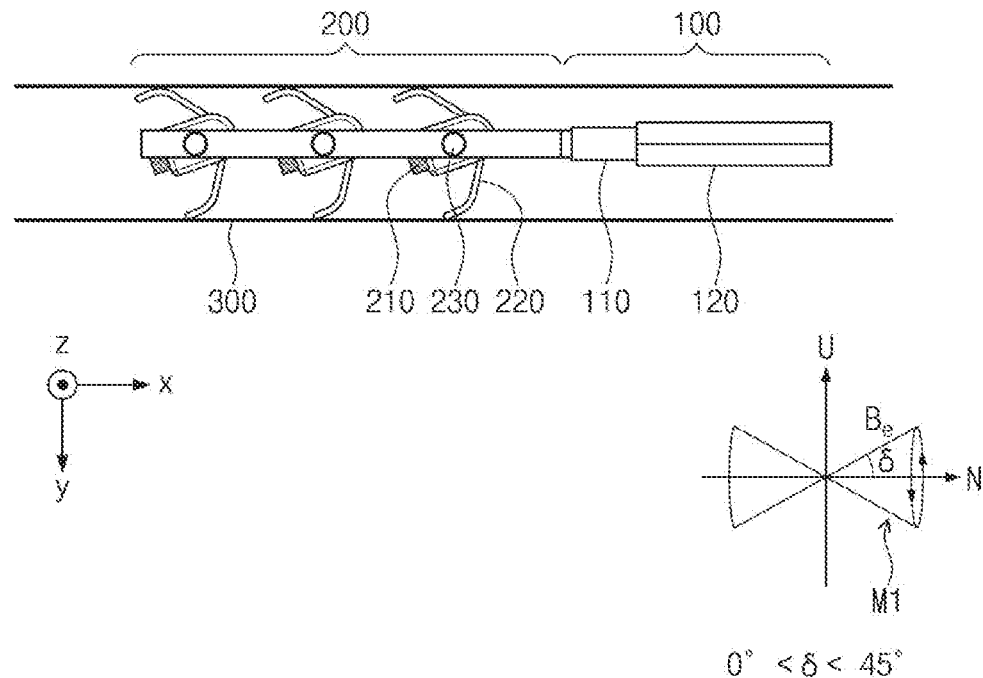
[Fig. 5]
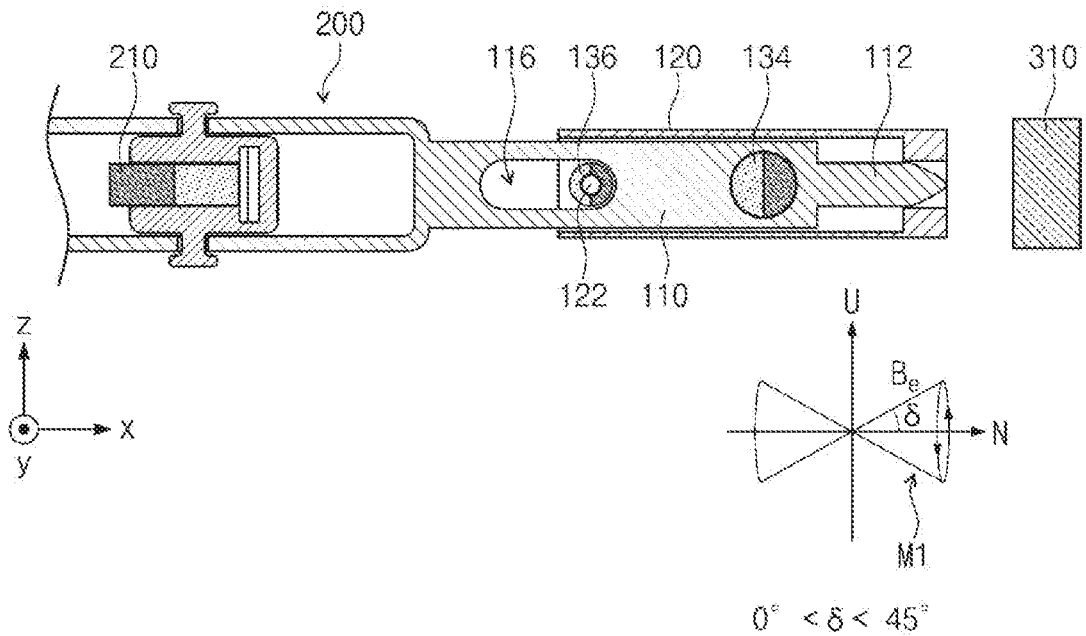

[Fig. 6]
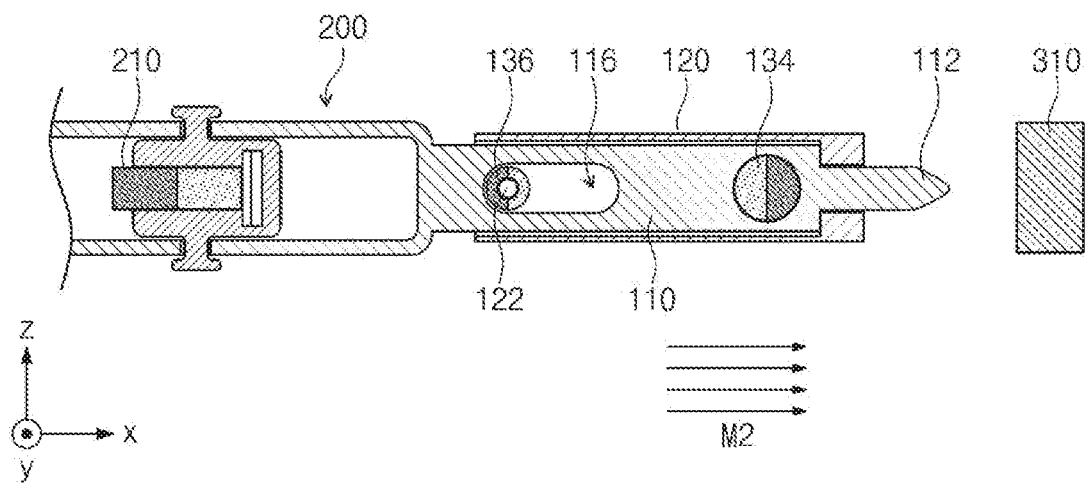
[Fig. 7]
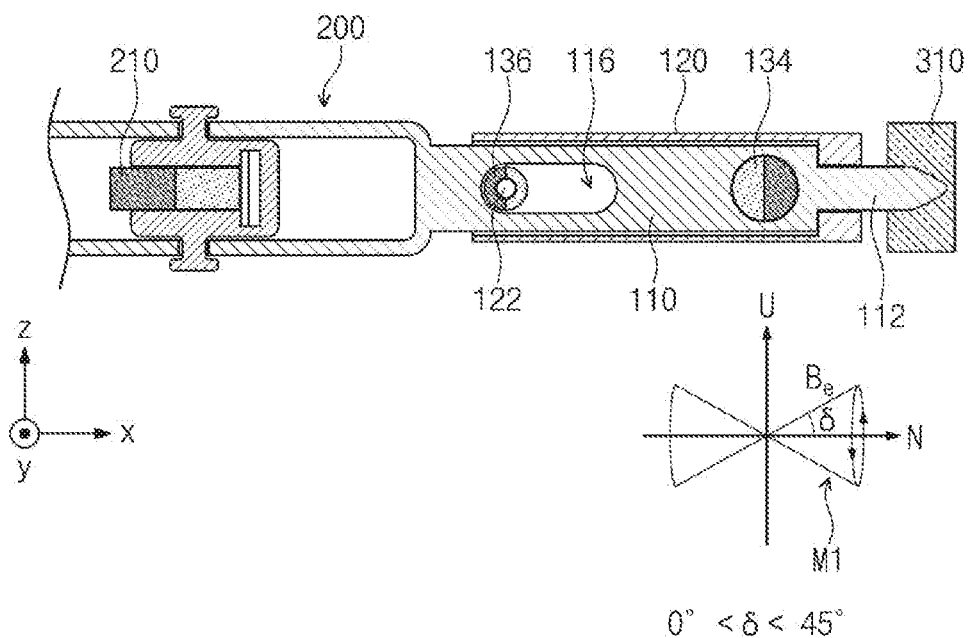

[Fig. 8]
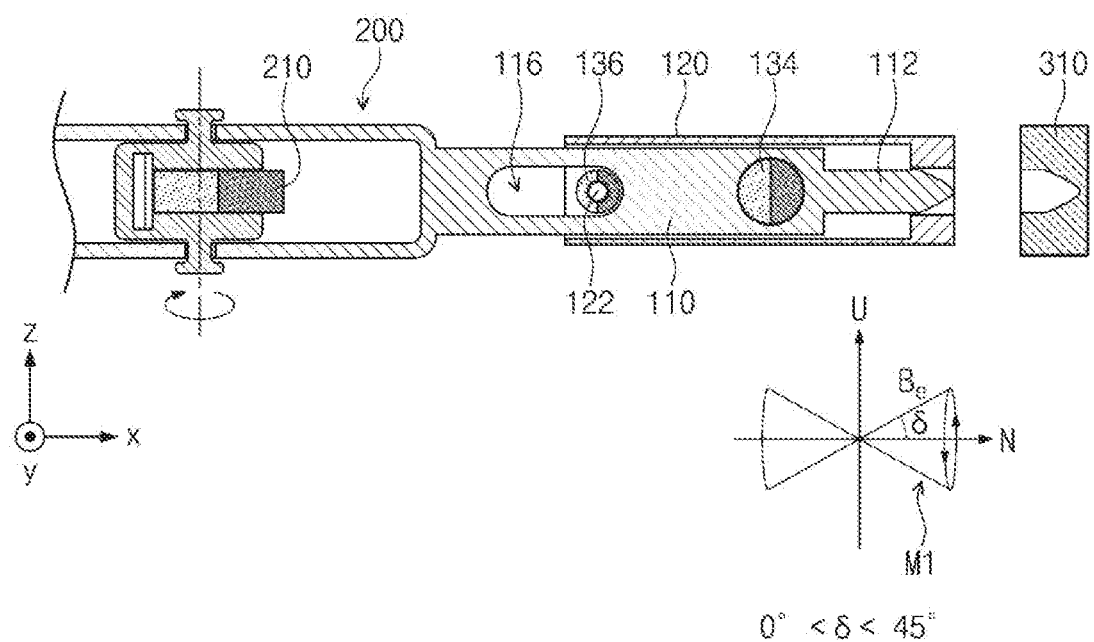
$0° < \delta < 45°$

MAGNETIC ROBOT

CROSS REFERENCE TO RELATED APPLICATIONS

This application is a National Stage of International Application No. PCT/KR2018/003911 filed Apr. 3, 2018, claiming priority based on Korean Patent Application No. 10-2017-0094167 filed Jul. 25, 2017.

TECHNICAL FIELD

The present invention relates to a magnetic robot, and more particularly, to a magnetic robot capable of collecting a body tissue under a control of an external magnetic field.

BACKGROUND ART

When performing a biopsy of a human body part, which is difficult to reach with an injection needle, a scalpel, or the like, such as a digestive organ or a heart, an endoscope, a catheter, or the like with a forceps is generally used. However, when using such wired tools, a patient may be infected with external bacteria intruded through a wire, which may lead to death if the patient has a weak immune system.

Recently, a wireless-driven magnetic robot developed to overcome disadvantages of such wired tools is focused on collecting a tissue of a digestive organ, while the magnetic robot has a limit to an operating time because the magnetic robot uses a motor using a small battery, and has disadvantage in that the robot moves inactively in a body.

However, in order to replace an existing biopsy, the robot has to be actively movable, and continuous biopsy is required.

Therefore, there is a demand for technologies for a wirelessly-driven magnetic robot that may easily perform a precise movement in the body and may ensure stability.

DISCLOSURE

Technical Problem

A technical object of the present invention is to provide a magnetic robot capable of selectively performing a movement and a tissue collection in a body tissue under a control of an external magnetic field.

The technical objects of the present invention are not limited to the above-described objects.

Technical Solution

In order to achieve the technical objects, the present invention provides a magnetic robot.

In accordance with one embodiment of the present invention, the magnetic robot includes: a moving part which is movable under a control of an external magnetic field; and an inspection part coupled to a front end of the moving part, wherein the inspection part includes: a body provided at a front end thereof with a tissue sampling needle; a cover for covering the body; and a cover-moving part for moving the cover between a first position and a second position, and the tissue sampling needle is accommodated in the cover when the cover is located in the first position, and the tissue sampling needle is exposed to an outside of the cover when the cover is located in the second position.

According to one embodiment, the body may have a first accommodation part formed at a position adjacent to the tissue sampling needle and a second accommodation part formed at a position adjacent to the inspection part, the cover-moving part may include: a fixed magnet inserted into the first accommodation part such that rotation of the fixed magnet is restricted; and a rotating magnet located in the second accommodation part and freely rotatable about a coupling shaft of the cover under the control of the external magnetic field, and the cover may be located in the first position as the rotating magnet moves toward the tissue sampling needle by an attractive force between the fixed magnet and the rotating magnet, and located in the second position as the rotating magnet moves toward the inspection part by a repulsive force between the fixed magnet and the rotating magnet.

According to one embodiment, the second accommodation part may be formed between the inspection part and the fixed magnet with a predetermined length, the rotating magnet may be located in one region of the second accommodation part, which is adjacent to the fixed magnet, when the cover is located in the first position, and the rotating magnet may be located in an opposite region of the second accommodation part, which is adjacent to the inspection part, when the cover is located in the second position.

According to one embodiment, the fixed magnet may be disposed such that one of an N-pole and an S-pole is adjacent to the tissue sampling needle, and a remaining one of the N-pole and the S-pole is adjacent to the rotating magnet.

According to one embodiment, the rotating magnet may have a ring shape, and may be bisected about the coupling shaft into an N-pole on one side and an S-pole on an opposite side.

According to one embodiment, the moving part may include a moving magnet controlled by the external magnetic field, and a magnetic force between the rotating magnet and the fixed magnet may be greater than a magnetic force between the rotating magnet and the moving magnet.

According to one embodiment, the tissue sampling needle may have a hook shape having a pointed tip, and the tissue sampling needle may penetrate into a forward tissue when the body moves forward, and the tissue sampling needle may collect the tissue when the body moves rearward.

Advantageous Effects

In the magnetic robot according to an embodiment of the present invention, the rotating magnet is rotated by applying the external magnetic field, so that the tissue sampling needle can be accommodated in the cover or exposed to the outside of the cover by using the attractive force or the repulsive force generated between the rotating magnet and the fixed magnet. While the magnetic robot moves in a blood vessel, the tissue sampling needle can be accommodated in the cover, so that an inner wall of the blood vessel can be prevented from being damaged by the tissue sampling needle during the movement.

The magnetic robot according to an embodiment of the present invention includes the inspection part and the moving part, and the inspection part is provided at a front end thereof with the tissue sampling needle having a hook-shaped tip, so that the tissue sampling needle can penetrate into the tissue when the moving part moves forward, and the tissue sampling needle can collect the tissue when the moving part moves rearward.

DESCRIPTION OF DRAWINGS

FIG. 1 is a perspective view showing a magnetic robot according to an embodiment of the present invention.

FIG. 2 is an exploded perspective view showing an inspection part the magnetic robot according to the embodiment of the present invention.

FIGS. 3(A) and 3(B) are sectional views showing the inspection part of the magnetic robot according to the embodiment of the present invention.

FIG. 4 is a view for describing a movement of the magnetic robot according to the embodiment of the present invention.

FIGS. 5 to 8 are views for describing tissue collection of the magnetic robot according to the embodiment of the present invention.

BEST MODE

The magnetic robot according to the present invention includes: a moving part which is movable under a control of an external magnetic field; and an inspection part coupled to a front end of the moving part, wherein the inspection part includes: a body provided at a front end thereof with a tissue sampling needle; a cover for covering the body; and a cover-moving part for moving the cover between a first position and a second position, and the tissue sampling needle is accommodated in the cover when the cover is located in the first position, and the tissue sampling needle is exposed to an outside of the cover when the cover is located in the second position.

MODE FOR INVENTION

Hereinafter, exemplary embodiments of the present invention will be described in detail with reference to the accompanying drawings. However, the technical idea of the present invention is not limited to the embodiments, but may be realized in different forms. The embodiments introduced herein are provided to sufficiently deliver the spirit of the present invention to those skilled in the art so that the disclosed contents may become thorough and complete.

When it is mentioned in the present disclosure that one element is on another element, it means that a first element may be directly formed on a second element, or a third element may be interposed between the first element and the second element. Further, in the drawings, thicknesses of membranes and areas are exaggerated for efficient description of the technical contents.

In addition, in the various embodiments of the present disclosure, the terms such as first, second, and third are used to describe various elements, but the elements are not limited to the terms. The terms are used only to distinguish one element from another element. Accordingly, an element mentioned as a first element in one embodiment may be mentioned as a second element in another embodiment. The embodiments described and illustrated herein include their complementary embodiments. Further, the term "and/or" in the present disclosure is used to include at least one of the elements enumerated before and after the term.

In the present disclosure, the terms of a singular form may include plural forms unless the context clearly indicates otherwise. Further, the terms such as "including" and "having" are used to designate the presence of features, numbers, steps, elements, or combinations thereof described in the present disclosure, and shall not be construed to preclude any possibility of presence or addition of one or more other features, numbers, steps, elements, or combinations thereof.

Further, in the following description of the present invention, a detailed description of known functions and configurations incorporated herein will be omitted when it may make the subject matter of the present invention unnecessarily unclear.

FIG. 1 is a perspective view showing a magnetic robot according to an embodiment of the present invention, FIG. 2 is an exploded perspective view showing an inspection part of the magnetic robot according to the embodiment of the present invention, and FIGS. 3(A) and 3(B) are sectional views showing the inspection part of the magnetic robot according to the embodiment of the present invention.

Referring to FIGS. 1 and 2, a magnetic robot may be inserted into tubular organs (bronchus, esophagus, stomach, intestine, urinary bladder, ureter, and blood vessels) in a human body to move in the tubular organs, and may collect a tissue for a biopsy.

The magnetic robot may include an inspection part 100 and a moving part 200, in which the inspection part 100 may be configured to collect the tissue for the biopsy, and may include a body 110, a tissue sampling needle 112, a cover 120, and a cover-moving part 130.

The body 110 may be provided at a front end thereof with the tissue sampling needle 112, and the body 110 may have a first accommodation part 114 and a second accommodation part 116.

The tissue sampling needle 112 may have a hook shape having a pointed tip. When the tissue sampling needle 112 is exposed to an outside of the cover 120, the tissue sampling needle 112 may penetrate into a forward tissue as the body 110 moves forward, and the tissue sampling needle 112 may collect the tissue as the body 110 moves rearward.

The first accommodation part 114 may be formed at a position adjacent to the tissue sampling needle 112. The first accommodation part 114 may provide a space in which a fixed magnet 134 is accommodated, and may have an inner diameter corresponding to a diameter of the fixed magnet 134.

The second accommodation part 116 may be formed on a rear side of the first accommodation part 114. The second accommodation part 116 may have a predetermined length in a longitudinal direction of the body 110. The second accommodation part 116 may provide a space into which a rotating magnet 136 is inserted, and a length of the second accommodation part 116 in the longitudinal direction of the body 110 may be greater than a diameter of the rotating magnet 136.

The cover 120 may surround the body 110, and may include a coupling shaft 122. The coupling shaft 122 may pass through the second accommodation part 116, and may be inserted into a center of the rotating magnet 136.

The cover 120 may move between a first position and a second position by the cover-moving part 130. The tissue sampling needle 112 may be accommodated in the cover 120 at the first position, and the tissue sampling needle 112 may be exposed to the outside of the cover 120 at the second position.

The cover-moving part 130 may move the cover 120 between the first position and the second position. The cover-moving part 130 may include the fixed magnet 134 and the rotating magnet 136.

The fixed magnet 134 and the rotating magnet 136 may be provided such that an N-pole and an S-pole meet each other. In the drawings, a portion with a bright color may be described as the N-pole, and a portion with a dark color may be described as the S-pole.

The fixed magnet 134 may be inserted into the first accommodation part 114 such that rotation of the fixed magnet 134 is restricted. The fixed magnet 134 may be disposed such that one of the N-pole and the S-pole is adjacent to the tissue sampling needle 112, and the remaining one of the N-pole and the S-pole is adjacent to the rotating magnet 136. According to the embodiment, the S-pole of the fixed magnet 134 may be adjacent to the tissue sampling needle 112, and the N-pole of the fixed magnet 134 may be adjacent to the rotating magnet 136.

The rotating magnet 136 may be located in the second accommodation part 116, may rotate about the coupling shaft 122 by magnetic forces with an external magnetic field and the fixed magnet 134, and may move within the second accommodation part 116. The rotating magnet 136 may have a ring shape, and the coupling shaft 122 may penetrate the center of the rotating magnet 136. The rotating magnet 136 may be bisected about the coupling shaft 122 into an N-pole on one side and an S-pole on an opposite side, and may rotate about the coupling shaft 122. When the rotating magnet 136 moves within the second accommodation part 116, the cover 120 may move together with the rotating magnet 136 by the coupling shaft 122. In detail, when the rotating magnet 136 is adjacent to the fixed magnet 134 within the second accommodation part 116, the cover 120 may be located in the first position. In addition, when the rotating magnet 136 is adjacent to the moving part 200 within the second accommodation part 116, the cover 120 may be located in the second position.

Hereinafter, the rotation and movement of the rotating magnet 136 and the movement of the cover 120 according to the movement of the rotating magnet 136 will be described in detail with reference to FIGS. 3(A) and 3(B).

Referring to FIGS. 3(A) and 3(B), FIG. 3(A) is a sectional view showing a case in which the cover 120 is disposed in the first position, and FIG. 3(B) is a sectional view showing a case in which the cover 120 is disposed in the second position.

Referring to FIG. 3(A), due to a magnetic force between the fixed magnet 134 and the rotating magnet 136, the S-pole of the rotating magnet 136 and the N-pole of the fixed magnet 134 may be aligned to face each other, so that an attractive force may be generated between the rotating magnet 136 and the fixed magnet 134. The rotating magnet 136 may move toward the fixed magnet 134 by the attractive force so as to be located in one region of the second accommodation part 116, which is adjacent to the fixed magnet 134. As the rotating magnet 136 moves, the cover 120 may move together with the rotating magnet 136 so as to be disposed in the first position. When the cover 120 is disposed in the first position, the tissue sampling needle 112 may be accommodated in the cover 120.

Meanwhile, referring to FIG. 3(B), when a magnetic field is applied in an X-axis direction from the outside, the rotating magnet 136 may rotate about the coupling shaft 122 so as to be aligned in a direction of the external magnetic field. In this case, the magnetic field applied from the outside may be transmitted to the rotating magnet 136 with a magnetic force having a magnitude greater than a magnitude of the magnetic force between the rotating magnet 136 and the fixed magnet 134. Accordingly, the N-pole of the rotating magnet 136 may be arranged to face the N-pole of the fixed magnet 134, so that a repulsive force may be generated between the rotating magnet 136 and the fixed magnet 134. The repulsive force may move the rotating magnet 136 toward the moving part 200, so that the rotating magnet 136 may be located in an opposite region of the second accommodation part 116, which is adjacent to the moving part 200. As the rotating magnet 136 moves and is located in the opposite region of the second accommodation part 116, the cover 120 moves together with the rotating magnet 136 so as to be disposed in the second position. When the cover 120 is disposed in the second position, the tissue sampling needle 112 may be exposed to the outside of the cover 120 to collect the tissue.

Referring again to FIG. 1, the moving part 200 may be configured to move the magnetic robot in the body, and may be moved under a control of the external magnetic field. The moving part 200 may be coupled to a rear side of the inspection part 100, and may include a moving magnet 210, a leg member 220, and a connection member 230.

The moving magnet 210 may be controlled by the external magnetic field to move, and the leg member 220 may move together with the moving magnet 210 as the moving magnet 210 moves. For example, when a precession magnetic field is applied from the outside, the moving magnet 210 may repeatedly rotate about a Z-axis within a predetermined angle range. The leg member 220 moves together with the moving magnet 210 according to such a movement of the moving magnet 210, and the moving part 200 may move forward by a friction between the leg member 220 and a body tissue.

Meanwhile, when the moving part 200 is to move rearward, the moving magnet 210 may rotate about the Z-axis by 180° under the control of the external magnetic field. Accordingly, arrangement of an iv-pole and an 2-pole of the moving magnet 210 may become opposite to arrangement of the N-pole and the-S pole of the moving magnet in the case where the moving part 200 moves forward. Thereafter, when an external precession magnetic field is applied, the leg member 220 moves together with the moving magnet 210 as the moving magnet 210 moves, and the moving part 200 may move rearward by the friction between the leg member 220 and the body tissue.

The leg member 220 may be formed of an elastic material, and an edge of the leg member 220 may have a blunt shape. In detail, the leg member 220 may be formed of a plate having a curvature. For example, the leg member 220 may be formed of a thin plate formed of a metal or plastic material which is bent and has elasticity, or thin silicon.

Since the leg member 220 is formed of an elastic material, when the magnetic robot is inserted into the human body, for example, into a blood vessel, appropriate contact may be maintained between the leg member 220 and the blood vessel without being affected by a size of the blood vessel. Therefore, the leg member 220 may stably support an inner wall of the blood vessel to stably maintain a position even with an external resistance and to flexibly move even if a size of an insertion target blood vessel is somewhat large or small.

The connection member 230 may connect the moving magnet 210 to the leg member 220. Due to the connection member 230, the movement caused by the rotation of the moving magnet 210 may be transferred to the leg member 220, and the leg member 220 may move to move the body 110.

Hereinafter, the movement of the magnetic robot by the moving part 200 will be described in detail with reference to FIG. 4.

FIG. 4 is a view for describing a movement of the magnetic robot according to the embodiment of the present invention.

Referring to FIG. 4, when the external precession magnetic field is applied to the moving magnet 210, the moving member 210 may rotate to allow the leg member 220 to move, and a frictional force may be generated between the leg member 220 and the inner wall of the blood vessel as the leg member 220 moves, so that the body 110 may move by the frictional force.

In detail, when an external precession magnetic field that rotates in a counterclockwise direction is applied to the moving magnet 210, a frictional force between one portion of the member 220 extending in a (−y)-axis direction and the inner wall of the blood vessel may be smaller than a frictional force between an opposite portion of the leg member 220 extending in a (+y)-axis direction and the inner wall of the blood vessel, and the two frictional forces may be formed in opposite directions.

Meanwhile, when an external precession magnetic field that rotates in a clockwise direction is applied to the moving magnet 210, a frictional force between the one portion of the leg member 220 and the inner wall of the blood vessel may be greater than a frictional force between the opposite portion of the leg member 220 and the inner wall of the blood vessel, and the two frictional forces may be formed in opposite directions.

The body 110 may move in a direction of a net frictional force which is the sum of the two frictional forces.

FIGS. 5 to 8 are views for describing tissue collection of the magnetic robot according to the embodiment of the present invention.

Referring to FIG. 5, the moving part 200 may move and reach a target tissue 310 by the precession magnetic field applied from the outside. During the movement of the moving part 200, a magnetic torque exerted on the rotating magnet 136 by the external magnetic field may be smaller than a magnetic torque formed by the fixed magnet 134 and the moving magnet 210. In addition, in the magnetic torque exerted on the rotating magnet 136, a magnetic torque formed with the fixed magnet 134 may be greater than a magnetic torque formed with the moving magnet 210. Therefore, the S-pole of the rotating magnet 136 and the N-pole of the fixed magnet 134 may be aligned to face each other by the magnetic force between the rotating magnet 136 and the fixed magnet 134, and an attractive force may be generated between the rotating magnet 136 and the fixed magnet 134. Accordingly, the cover 120 may be located in the first position, and the tissue sampling needle 112 may be accommodated in the cover 120.

Referring to FIG. 6, as a magnetic field is applied in a (+X)-axis direction from the outside, the rotating magnet 136 may rotate about a y-axis so as to be aligned in the direction of the external magnetic field. In this case, the magnetic torque exerted on the rotating magnet 136 by the external magnetic field may be greater than the magnetic torque formed by the fixed magnet 134 and the moving magnet 210. Therefore, the rotating magnet 136 may be magnetized in the (+X)-axis direction so that the N-pole of the rotating magnet 136 may be arranged to face the N-pole of the fixed magnet 134. Accordingly, a repulsive force may be generated between the rotating magnet 136 and the fixed magnet 134. The repulsive force may move the rotating magnet 136 toward the moving part 200, the cover 120 may move together with the rotating magnet 136 so as to be located in the second position, and the tissue sampling needle 112 may be exposed to the outside.

Referring to FIG. 7, a precession magnetic field may be applied from the outside so that the moving part 200 may move forward. Accordingly, the tissue sampling needle 112 may penetrate into the target tissue 310.

Referring to FIG. 8, when the tissue sampling needle 112 sufficiently penetrates into the target tissue 310, an external magnetic field may be applied in a (−X)-axis direction, so that the moving magnet 210 may rotate about the Z-axis by 180°.

Thereafter, a precession magnetic field may be applied from the outside so that the moving part 200 may move rearward. While the precession magnetic field is applied, the rotating magnet 136 may rotate about the y-axis by magnetic forces with the fixed magnet 134 and the moving magnet 210, so that the S-pole of the rotating magnet 136 and the N-pole of the fixed magnet 134 may be aligned to face each other, and the N-pole of the rotating magnet 136 and the S-pole of the moving magnet 210 may be aligned to face each other. An attractive force may be generated between the rotating magnet 136 and the fixed magnet 134 and between the rotating magnet 136 and the moving magnet 210, in which the attractive force between the rotating magnet 136 and the fixed magnet 134 may be stronger than the attractive force between the rotating magnet 136 and the moving magnet 210. Therefore, the rotating magnet 136 may move toward the fixed magnet 134. As the rotating magnet 136 moves, the cover 120 may be located in the first position, and the tissue sampling needle 112 may be accommodated in the cover 120 again. The moving part 200 may move rearward while the tissue sampling needle 112 is accommodated in the cover 120.

Magnetic torques exerted on the rotating magnet 136 and the moving magnet 210 controlled by the magnetic field applied from the outside may be calculated through Mathematical formulas 1 to 4 below.

When the external magnetic field is applied, the magnetic torque exerted on the rotating magnet 136 may be defined by Mathematical formula 1 below.

$$T = m \times B \quad \text{[Mathematical formula 1]}$$

(T is the magnetic torque exerted on the rotating magnet, m is a magnetic moment of the rotating magnet, and B is the external magnetic field)

The external precession magnetic field may be defined by Mathematical formula 2 below.

$$B_e = B_e(\cos(\delta)N + \sin\delta\,\cos(2\pi ft)U + \sin\delta\,\sin(2\pi ft)N \times U) \quad \text{[Mathematical formula 2]}$$

($B_e$ is intensity the external precession magnetic field, f is a frequency of the external precession magnetic filed, t is a time, N is a rotation axis vector, and U is a normal vector of N)

The magnetic field generated by the moving magnet 210 may be defined by Mathematical formula 3 below.

$$B_{point\text{-}dipole} = \frac{\mu_0}{4\pi}\left(\frac{3R(m \cdot R)}{R^5} - \frac{m}{R_3}\right) \quad \text{[Mathematical formula 3]}$$

($\mu_0$ is permeability of a space, R is a vector from the moving magnet to an arbitrary point, and R is a magnitude of R)

Through Mathematical formula 1 described above and Mathematical formula 4 below, a condition of an external magnetic field for moving the cover 120 may be set.

$$F = (m \cdot \nabla)B \quad \text{[Mathematical formula 4]}$$

(F is a force exerted by the external magnetic field or the moving magnet, and B is a magnetic field generated by the external magnetic field or the moving magnet)

When no external magnetic field is applied, or the intensity of the external magnetic field is small, the magnetic torque exerted on the rotating magnet 136 by the external magnetic field may be smaller than the magnetic torques formed by the fixed magnet 134 and the moving magnet 210, so that the rotating magnet 136 may be magnetized in the (−x)-axis direction. Accordingly, the cover 120 may be disposed in the first position, so that the tissue sampling needle 112 may be accommodated in the cover 120.

When the external magnetic field is applied, or the intensity of the external magnetic field is increased, the magnetic torque exerted on the rotating magnet 136 by the external magnetic field may be greater than the magnetic torques formed by the fixed magnet 134 and the moving magnet 210, so that the rotating magnet 136 may be magnetized in the (+x)-axis direction. Accordingly, the cover 120 may be disposed in the second position, so that the tissue sampling needle 112 may be exposed to the outside of the cover 120.n Although the exemplary embodiments of the present invention have been described in detail, the scope of the present invention is not limited to a specific embodiment, and should be interpreted by the appended claims. In addition, it should be understood by those skilled in the art to which the invention pertains that various changes and modifications can be made without departing from the scope of the present invention.

INDUSTRIAL APPLICABILITY

The present invention may be applied to the collection of body tissues in tubular tissues of a human body, such as blood vessels, digestive organs, and urethra.

The invention claimed is:

1. A magnetic robot comprising:
a moving part which is movable under a control of an external magnetic field; and
an inspection part coupled to a front end of the moving part,
wherein the inspection part includes:
a body provided at a front end thereof with a tissue sampling needle;
a cover for covering the body; and
a cover-moving part for moving the cover between a first position and a second position,
the tissue sampling needle is accommodated in the cover when the cover is located in the first position, and the tissue sampling needle is exposed to an outside of the cover when the cover is located in the second position,
the body has a first accommodation part formed at a position adjacent to the tissue sampling needle and a second accommodation part formed at a position adjacent to the inspection part,
the cover-moving part includes:
a fixed magnet inserted into the first accommodation part such that rotation of the fixed magnet is restricted; and
a rotating magnet located in the second accommodation part and freely rotatable about a coupling shaft of the cover under the control of the external magnetic field,
the cover is located in the first position as the rotating magnet moves toward the tissue sampling needle by an attractive force between the fixed magnet and the rotating magnet, and located in the second position as the rotating magnet moves toward the inspection part by a repulsive force between the fixed magnet and the rotating magnet,
the second accommodation part is formed between the inspection part and the fixed magnet with a predetermined length,
the rotating magnet is located in one region of the second accommodation part, which is adjacent to the fixed magnet, when the cover is located in the first position, and
the rotating magnet is located in an opposite region of the second accommodation part, which is adjacent to the inspection part, when the cover is located in the second position.

2. The magnetic robot of claim 1, wherein the fixed magnet is disposed such that one of an N-pole and an S-pole is adjacent to the tissue sampling needle, and a remaining one of the N-pole and the S-pole is adjacent to the rotating magnet.

3. The magnetic robot of claim 1, wherein the rotating magnet has a ring shape, and is bisected about the coupling shaft into an N-pole on one side and an S-pole on an opposite side.

4. The magnetic robot of claim 1, wherein the moving part includes a moving magnet controlled by the external magnetic field, and
a magnetic force between the rotating magnet and the fixed magnet is greater than a magnetic force between the rotating magnet and the moving magnet.

5. The magnetic robot of claim 1, wherein the tissue sampling needle has a hook shape having a pointed tip, and
the tissue sampling needle penetrates into a forward tissue when the body moves forward, and the tissue sampling needle collects the tissue when the body moves rearward.

* * * * *